(12) United States Patent
Muller et al.

(10) Patent No.: US 9,968,469 B2
(45) Date of Patent: May 15, 2018

(54) PROSTHESIS LINER WITH SUCTION CUP AND VACUUM LOCK MECHANISM

(71) Applicant: OTTO BOCK HEALTHCARE GMBH, Duderstadt (DE)

(72) Inventors: Andre Muller, Duderstadt (DE); Martin Hillmann, Duderstadt (DE)

(73) Assignee: OTTO BOCK HEALTHCARE GMBH, Duderstadt (DE)

( * ) Notice: Subject to any disclaimer, the term of this patent is extended or adjusted under 35 U.S.C. 154(b) by 0 days. days.

(21) Appl. No.: 14/424,394

(22) PCT Filed: Aug. 29, 2013

(86) PCT No.: PCT/EP2013/002595
§ 371 (c)(1),
(2) Date: Feb. 26, 2015

(87) PCT Pub. No.: WO2014/032802
PCT Pub. Date: Mar. 6, 2014

(65) Prior Publication Data
US 2015/0202060 A1 Jul. 23, 2015

(30) Foreign Application Priority Data

Aug. 31, 2012 (DE) .......................... 10 2012 017 214

(51) Int. Cl.
*A61F 2/78* (2006.01)
*A61F 2/80* (2006.01)
*A61F 2/74* (2006.01)

(52) U.S. Cl.
CPC .............. *A61F 2/80* (2013.01); *A61F 2/7812* (2013.01); *A61F 2002/742* (2013.01);
(Continued)

(58) Field of Classification Search
CPC ........ A61F 2/78; A61F 2/7812; A61F 2/7843; A61F 2/80; A61F 2002/5007;
(Continued)

(56) References Cited

U.S. PATENT DOCUMENTS 1,865,957 A 7/1932 Priest
2,319,727 A * 5/1943 Duggan .................. F16B 47/00
248/205.9
(Continued)

FOREIGN PATENT DOCUMENTS

DE 10128234 A1 1/2003
DE 10142491 A1 4/2003
(Continued)

OTHER PUBLICATIONS

PCT International Search Report for PCT International Application No. PCT/EP2013/002595, dated Nov. 21, 2013.
(Continued)

*Primary Examiner* — Thomas J Sweet
*Assistant Examiner* — Christie Bahena
(74) *Attorney, Agent, or Firm* — Holland & Hart

(57) ABSTRACT

A prosthesis liner for placing on a stump includes an elastic main body which has a proximal opening for inserting the stump into a receiving space, and a distal end. At least one suction cup is arranged on the outside of the prosthesis liner.

24 Claims, 12 Drawing Sheets

(52) U.S. Cl.
CPC ... *A61F 2002/747* (2013.01); *A61F 2002/785* (2013.01); *A61F 2002/7818* (2013.01); *A61F 2002/805* (2013.01)

(58) Field of Classification Search
CPC .......... A61F 2002/742; A61F 2002/785; A61F 2002/802; A61F 2002/805; A61F 2002/807; A61F 2002/7818; A61F 2002/7875; A61F 2/76; F16B 47/00
See application file for complete search history.

(56) References Cited

U.S. PATENT DOCUMENTS

| | | | | |
|---|---|---|---|---|
| 3,325,639 | A | * | 6/1967 | King .................. F16B 47/00 174/117 R |
| 5,133,524 | A | * | 7/1992 | Liu .................... F16B 47/00 248/205.8 |
| 5,213,385 | A | * | 5/1993 | Nagai .................. B65G 47/91 294/189 |
| 5,662,715 | A | * | 9/1997 | Slemker .................. A61F 2/76 623/33 |
| 5,830,237 | A | * | 11/1998 | Kania .................. A61F 2/7812 2/22 |
| 5,888,230 | A | * | 3/1999 | Helmy .................. A61F 2/7812 602/62 |
| 6,206,932 | B1 | * | 3/2001 | Johnson .................. A61F 2/68 623/38 |
| 6,797,008 | B1 | | 9/2004 | Arbogast et al. |
| 7,118,602 | B2 | * | 10/2006 | Bjarnason .......... A61F 2/7812 602/26 |
| 7,144,429 | B2 | | 12/2006 | Carstens |
| 8,052,760 | B2 | | 11/2011 | Egilsson et al. |
| 9,155,636 | B1 | * | 10/2015 | Fikes .................... A61F 2/80 |
| 2002/0185575 | A1 | | 12/2002 | Kalb |
| 2005/0240282 | A1 | * | 10/2005 | Rush .................... A61F 2/60 623/26 |
| 2005/0267598 | A1 | | 12/2005 | Bjarnason et al. |
| 2008/0243266 | A1 | * | 10/2008 | Haynes ................ A61F 2/68 623/34 |
| 2008/0269914 | A1 | * | 10/2008 | Coppens .............. A61F 2/5046 623/33 |
| 2010/0070051 | A1 | | 3/2010 | Carstens |
| 2010/0094432 | A1 | * | 4/2010 | Mackenzie ............ A61F 2/68 623/34 |
| 2011/0035027 | A1 | | 2/2011 | McCarthy |
| 2011/0077748 | A1 | | 3/2011 | Egilsson et al. |
| 2012/0191217 | A1 | | 7/2012 | Mackenzie |
| 2012/0191218 | A1 | | 7/2012 | McCarthy |
| 2013/0123940 | A1 | * | 5/2013 | Hurley .................. A61F 2/80 623/33 |

FOREIGN PATENT DOCUMENTS

| | | |
|---|---|---|
| DE | 10153796 A1 | 6/2003 |
| DE | 102004050201 A1 | 4/2006 |
| RU | 2411020 C2 | 2/2011 |
| WO | 2012051385 A1 | 4/2012 |

OTHER PUBLICATIONS

Examination report of corresponding Russian patent application No. 2015111156/14 dated Aug. 29, 2013; 2 pgs.

* cited by examiner

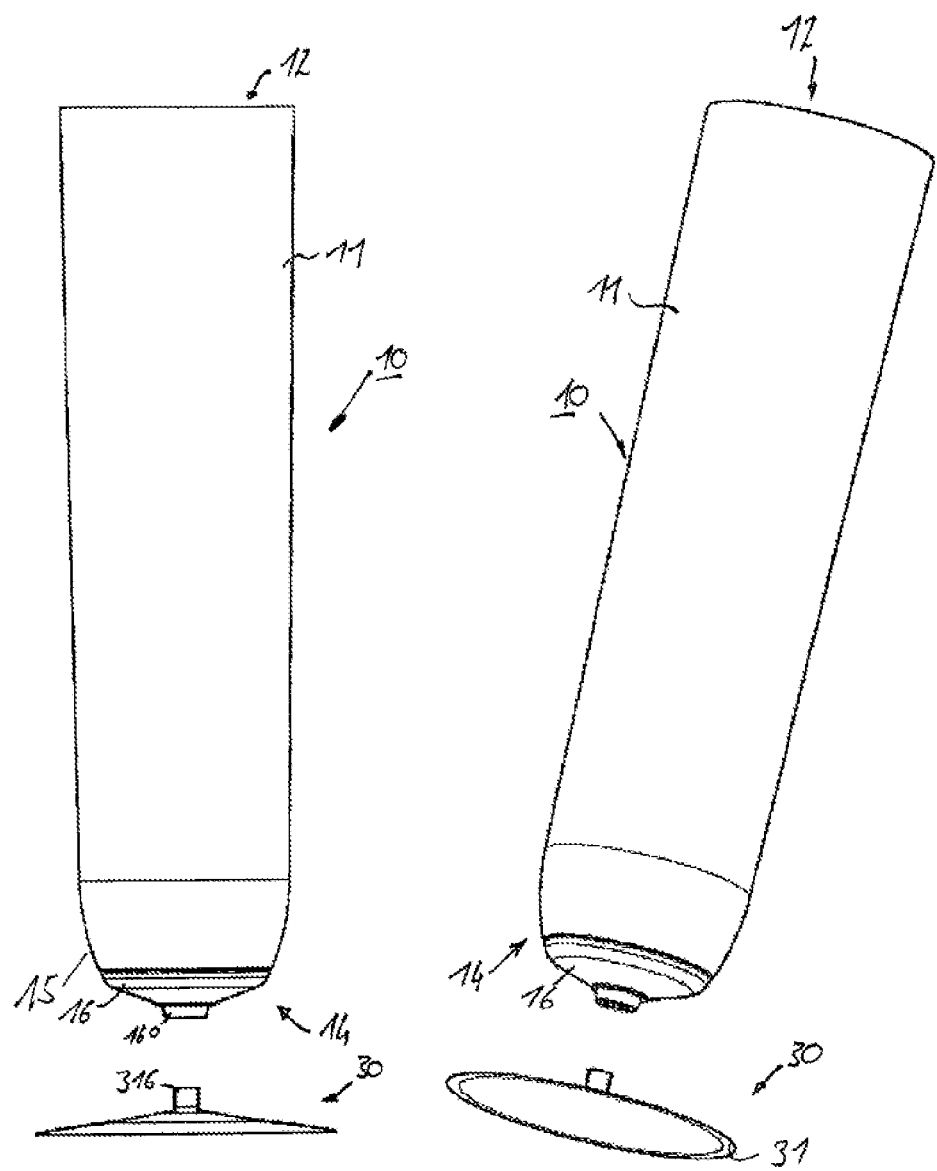

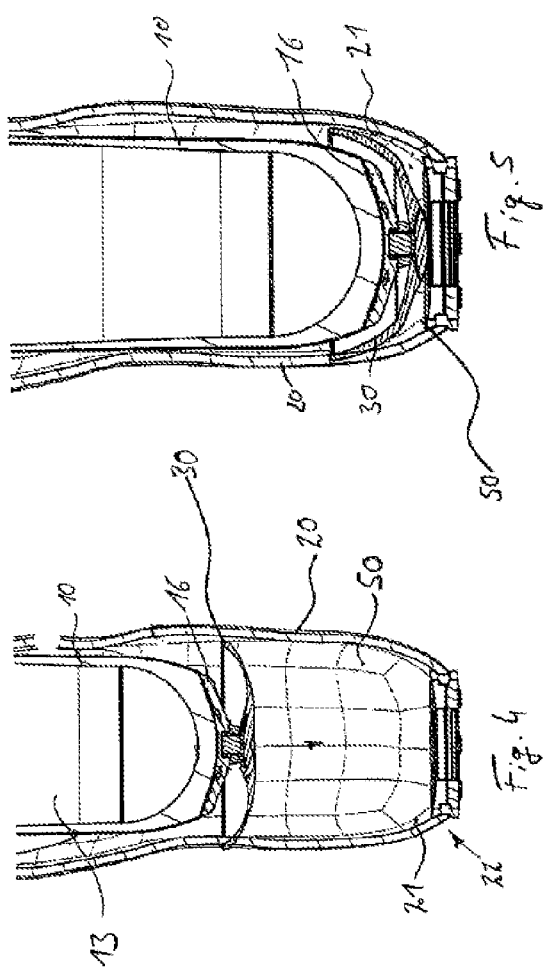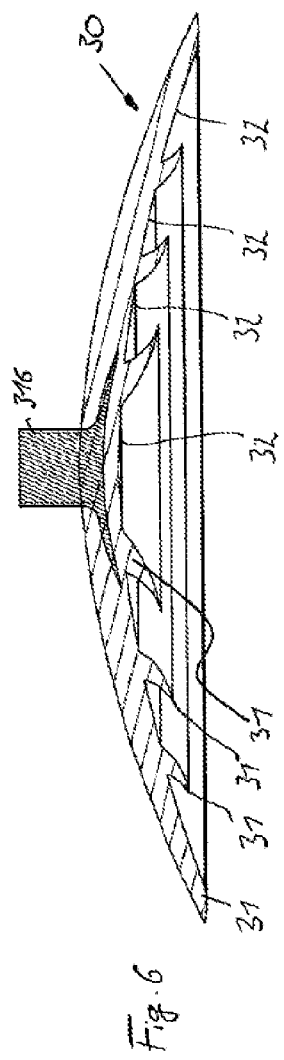

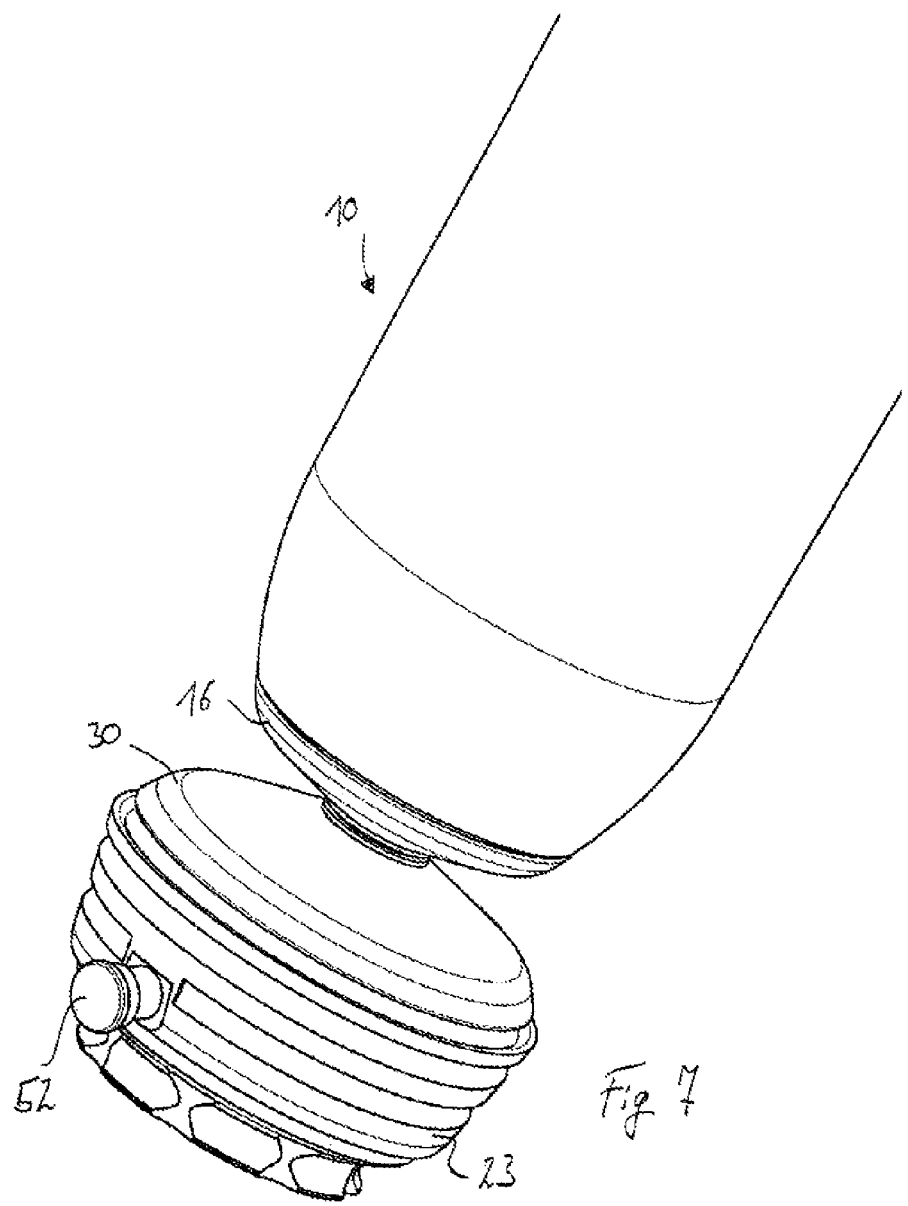

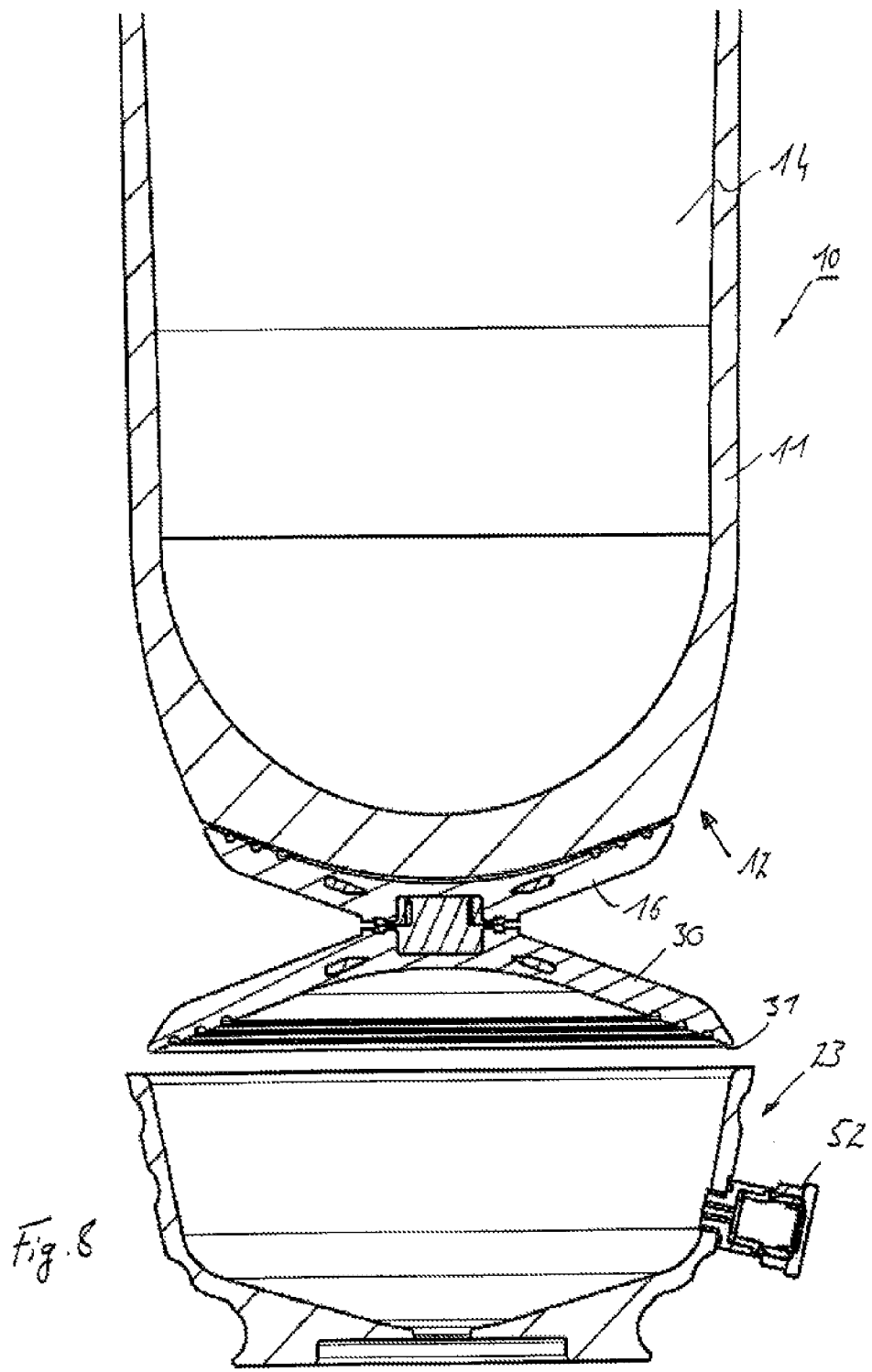

PROSTHESIS LINER WITH SUCTION CUP AND VACUUM LOCK MECHANISM

TECHNICAL FIELD

The invention relates to a prosthesis liner for placing on a stump, having an elastic main body which has a proximal opening for introducing the stump into a receiving space, and a distal end, and also to a prosthesis socket system having such a prosthesis liner and a prosthesis socket.

BACKGROUND

Prostheses serve to replace the function and optionally the visual appearance of a missing limb and are secured to the body of the patient. A large number of options are known for securing the prosthesis. A widespread option for securing prostheses to the extremities is that of arranging the prosthesis on a remaining part of the limb, referred to as the stump. The stump is surrounded by a prosthesis socket, which is generally dimensionally stable. An introduction opening is formed at the proximal end of the socket and at least one fastening device on which further prosthesis components can be arranged, for example joints or functional units such as prosthetic feet or prosthetic hands, is provided at the distal end of the socket. In order to achieve a good fit, a model of the stump is made and the socket is adapted to the contour of the stump model. In order to be able to compensate for fluctuations in volume, provision can be made for the socket to be manufactured in a narrower manner than the molded stump model.

In order to increase the wearing comfort, provision can be made for what is referred to as a prosthesis liner to be arranged between the prosthesis socket and the stump. The prosthesis liner generally consists of a closed main body having a proximal opening and is pulled in the manner of a sock over the stump. The elastic material adheres to the stump surface and establishes the connection between the stump and the prosthesis socket. In order to fasten the prosthesis liner to the prosthesis socket, provision can be made of mechanical locking elements at the distal end of the prosthesis liner and corresponding locking devices at the distal end of the prosthesis socket, said locking devices locking the prosthesis liner to the prosthesis socket in a form-fitting manner after fitting the stump into the prosthesis socket. An unlocking device can be used to undo the fastening of the prosthesis liner to the prosthesis socket.

A further option for fastening a prosthesis socket to a stump consists in what is referred to as suction socket liner technology, in which the prosthesis socket is sealed off with respect to the prosthesis liner in an airtight manner and the air present in the intermediate space between the prosthesis liner and the prosthesis socket is sucked or pushed out of said intermediate space. A return flow is prevented via a nonreturn valve. To this end, it is necessary to configure the prosthesis socket in an airtight manner and to ensure extensive sealing with respect to the prosthesis liner.

DE 101 53 796 A1 relates to a prosthesis socket and a prosthesis liner which has, at its distal end, a fixing member having a cylindrical peg which is provided with a rotationally symmetrical sawtooth profile. The peg is passed through an opening at the distal end of the prosthesis socket and is mechanically locked via a slide. At the distal end of the prosthesis liner, a sealing lip is arranged as a closed ring around the peg.

US 2011/0035027 A1 relates to a vacuum-assisted liner system having a flexible liner which is pulled over a stump and has at least one circumferential edge. The liner is produced from an air-impermeable material and has at least one porous region which is spaced apart from the circumferential edge, in order to allow the transport of air and moisture between an outer surface and an inner surface of the liner.

DE 101 42 491 A1 relates to a sealing arrangement for sealing off an amputation stump in a cup-shaped, airtight prosthesis socket having a tubular, elastic and airtight carrier which is able to be pulled onto the amputation stump and encloses the amputation stump on all sides in the circumferential direction. Arranged on the outer side of the carrier is a sealing lip which rests against the prosthesis socket in a sealing manner.

U.S. Pat. No. 8,052,760 B2 relates to a prosthesis liner for forming an interface between a stump and a prosthesis socket. The liner is formed in a substantially conical manner and produced from a material which is elastically deformable. The proximal end is open and the distal end is closed. At the outer circumference of the liner, separate sealing elements are fastened to the outer surface of the liner.

WO 2012/051385 A1 relates to a prosthesis liner as an interface between a stump and a prosthesis socket, in which at least one resilient sealing element extends radially outward and at least along a part of the circumference of the liner. A cushion for controlling the volume is arranged in the liner and pushes the sealing element outward.

US 2012/0191217 A1 relates to a socket system having a vacuum liner for prosthetic or orthotic devices. A region made of an elastic material is arranged on the closed liner at the distal end, said elastic material being harder than the material of the rest of the liner. The region has a concave section which extends inward from an outer end surface of the region. The distal region and the concave section form at least a part of a vacuum pump in order to pump air out of the intermediate space between the liner and the prosthesis socket.

SUMMARY

It is the object of the present invention to provide a prosthesis liner and a prosthesis socket with which fastening of the prosthesis is ensured even in the event of reduced fitting precision in the socket and fluctuations in volume have less of an influence on securing within the prosthesis socket.

According to the invention, this object is achieved by a prosthesis liner having the features of the main claim and a prosthesis socket system having the features of the additional independent claim. Advantageous configurations and developments of the invention are disclosed in the dependent claims, the figures and the description.

In the case of the prosthesis liner for placing on a stump, having an elastic main body which has a proximal opening for introducing the stump into a receiving space, and a distal end, provision is made for a suction cup to be arranged on the outer side of the prosthesis liner.

The suction cup makes it possible to establish the holding force between the prosthesis liner and the prosthesis socket with the aid of an additional element. To this end, negative pressure is generated in the region between the suction cup and the socket. Negative pressure is not applied to the liner itself, to be more precise, negative pressure is not necessarily applied in the volume between the prosthesis socket and the prosthesis liner, and so the fitting precision of a prosthesis socket is no longer decisive for the sealing of the connection between the prosthesis socket and the prosthesis liner and thus for the holding force of the prosthesis liner within the prosthesis socket. The suction cup can be arranged at the distal end of the liner. As a result of the arrangement of a suction cup at the distal end of the prosthesis liner, any desired liner can be used for fastening within a prosthesis socket, and particular requirements on the sealing and in particular the sealing capability with respect to the prosthesis socket are not imposed apart from the region of contact in the prosthesis socket. It is also possible and provision is made for one or more suction cups to be arranged in the front end region in addition to the arrangement of the suction cup at the front, that is to say distal end of the liner, such that the holding forces are distributed between a number of locations. The plurality of suction cups can be arranged in a manner distributed around the circumference on the outer side, for example in a symmetrical arrangement, and likewise a central suction cup can be supplemented by further suction cups arranged at the circumference.

The prosthesis socket itself can be formed in an extensively perforated manner so that ventilation can take place, and likewise liquids can pass into the volume between the prosthesis liner and the prosthesis socket and exit again through openings, without there being the risk of the prosthesis liner detaching from the prosthesis socket. Via a definition of the suction cup geometry it is possible to set the holding force exactly without the geometric conditions placed on the prosthesis socket or prosthesis liner having to be taken into consideration.

The suction cup or suction cups can be configured as a separate component and fastened to the prosthesis liner, and in particular the respective suction cup can be fastened reversibly to the distal end or in the distal end region of the prosthesis liner. As a result of a reversible fastening or fastening capability to the prosthesis liner, it is possible to fasten suction cups having different sizes to the liner in order to be able to make it possible to adapt to the holding force required in each case. It is likewise possible for suction cups adapted to a prosthesis socket to be able to be fitted on different prosthesis liners or for standard suction cups to be attached to individually manufactured prosthesis liners and prosthesis sockets. For reversibly fastening the suction cup to the prosthesis liner, at least one fastening device is formed on the prosthesis liner and correspondingly on the suction cup. The fastening device can be for example in the form of a screw system, a click system having a ball-head mounting, form-fitting locking via touch-and-close fasteners or a peg system having a corresponding receptacle and corresponding locking means.

In order to be able to ensure secure fastening of the suction cup to the prosthesis liner and furthermore to allow sufficient stability and force distribution from the distal end of the prosthesis liner to the stump, in one development of the invention a dimensionally stable end cap, to which the suction cup is secured, is provided at the distal end. Securing can take place via the above-described fastening devices. In principle, it is also possible for the suction cup to be integrally formed on the distal end of the prosthesis liner or the end cap so as to result in a very compact type of construction. Furthermore, on account of the elastic deformability of the suction cup, good and elastic support of the distal stump end within the prosthesis liner is provided. In the case of a one-piece configuration of the prosthesis liner having the suction cup, too, the functional separation between ensuring a sufficient holding force via the suction cup at the distal end and positioning and securing the prosthesis liner within the prosthesis socket is provided.

Instead of an allover vacuum solution, in which the volume between the prosthesis socket and the prosthesis liner is evacuated, according to the invention, the securing of the prosthesis liner within the prosthesis socket is provided only at the distal end via the suction cup.

The suction cup has at least one circumferential sealing lip via which the volume between the suction cup and the prosthesis socket is able to be sealed off. The circumferential sealing lip defines the sealing edge which rests permanently against the inner side of the prosthesis socket or a receiving device in order to maintain the necessary negative pressure. If the suction cup, which is made of an elastic material, for example a TPE, is introduced into the prosthesis socket, the pushing of the gas, usually air, out of the enclosed volume results in a negative pressure. Depending on the configuration both of the suction cup and of the prosthesis socket or of a receiving bowl, a part of the suction cup can turn over and press against the inner side of the prosthesis socket or the receiving device, with the result that a sealing edge is formed with respect to the socket. It is possible for a number of sealing edges to be formed on the underside of the suction cup, for example by the attachment or formation of a lamellar structure on the underside of the suction cup, said lamellar structure consisting of concentrically arranged lamellae. As a result, adaptation to different diameters or contours within the prosthesis socket can be achieved. Likewise, in the case of a multiple configuration of sealing edges or sealing lips, the security is increased in that at least one sealing lip is always in radially sealing contact with the inner side of the prosthesis socket.

Within the circumferential sealing lip or circumferential sealing lips, a roughened structure, a textile and/or a non-adhesive or air-permeable coating can be provided on the suction-cup surface, thereby ensuring that only the desired sealing lip forms a sealing edge and comes into sealing contact with the inner side of the prosthesis socket. This also ensures that the effective area of the vacuum is distributed extensively over the entire underside of the suction cup within the sealing lip. Sealing contact with the socket is prevented from accidentally arising at some other point on the underside, with the consequence that the holding force turns out to be smaller than desired.

Advantageously, the suction cup has a convex shape on the side facing away from the prosthesis liner, this having the result that the suction cup bears against the inner side of the prosthesis socket after it has been introduced into the prosthesis socket and the volume beneath the convex curvature has been pushed out. To this end, it is necessary for the outer periphery to turn over, with the result that a radially outwardly acting force is exerted on the outer periphery of the suction cup on account of the elastic restoring force. As a result of the turning over, additional mechanical locking is provided, since, in addition to the negative pressure, the mechanical restoring force also has to be overcome counter to the prosthesis liner being pulled out of the prosthesis socket. The suction cup advantageously has a shape and functionality which allows at least a peripheral region of the suction cup to turn over around the entire circumference, wherein advantageously a restoring force is applied by the suction cup, said restoring force urging the turned-over part of the suction cup back into the starting position.

A development of the invention provides for a fluidic connection to exist between the receiving space within the prosthesis liner and the suction cup. As a result, it is possible, by repeatedly loading and unloading the suction cup within the prosthesis socket, to effect a pump action between the receiving space of the prosthesis liner and the stump. As a result, it is possible to carry out an evacuation of the intermediate space between the prosthesis liner and the stump. Furthermore, it is possible to carry out an air exchange by way of regulated leakage within the liner. This results in increased skin compatibility since air and moisture can be transported out of the interior of the prosthesis liner.

A blocking device which prevents air or moisture from flowing back into the receiving space can be arranged within the fluidic connection between the receiving space for the stump and the suction cup. As a result, a vacuum or negative pressure can be achieved in a targeted manner within the prosthesis liner. The suction cup furthermore serves as a mechanical holder between the prosthesis socket and the prosthesis liner, and at the same time a secure seat of the prosthesis liner on the stump is possible as a result of targeted evacuation. By way of the blocking device, for example a nonreturn valve, the degree of evacuation can be set.

A section that provides sealing with respect to the stump can be formed at the proximal end of the prosthesis liner in order to achieve airtight and watertight contact at least of the proximal periphery of the liner with the stump. This upper, sealing section can be adjoined, distally thereto, by a region which is configured in a set-back manner, or such a region can be arranged distally thereto, such that a spaced-apart region or clearance is formed between the stump and the liner. Within this region, a rough structure, channels, a textile, a foam or an air-permeable coating can be provided, such that air circulation can take place within this region. It is likewise possible, by targeted evacuation of this region for example through the fluidic connection between the receiving space and the suction space, to realize targeted leakage and air exchange.

In the case of the prosthesis socket system having a prosthesis liner, as described above, and a prosthesis socket, provision is made for the prosthesis socket to have a contact region corresponding to the suction cup and for a closed volume to be formed between the suction cup and the contact region in the coupled state. The corresponding contact region is configured such that the suction cup can bear in a sealing manner against the inner side of the prosthesis liner along a sealing lip, in order to form a sealing edge, such that the surrounding medium, generally air, cannot pass into the closed volume. The closed volume has a negative pressure compared with the surrounding pressure, and so a holding force is applied via the suction cup, such that the prosthesis liner cannot be removed from the prosthesis socket. The negative pressure or the vacuum in the contact region can be achieved by introducing the suction cup into the prosthesis socket and mechanically pushing out at least a part of the enclosed air, but alternatively or in addition, provision can be made of a pump device, via which air is sucked out of the volume between the suction cup and the prosthesis socket.

In addition to the air being pushed laterally past the circumferential edge of the suction cup, it is possible for a blocking device or a fluidic connection to a blocking device to be present within the volume, this allowing air to flow out and preventing a return flow. This is possible for example by way of a nonreturn valve which can optionally also be opened in order to undo the locking. As a result of the arrangement of a blocking device, virtually noiseless evacuation is possible, and furthermore the particular location at which the air is pushed out of the volume can be defined.

The closed volume can be fluidically connected to an aeration device for introducing air, in order to lift the negative pressure in the closed volume and to be able to remove the prosthesis liner from the prosthesis socket. The aeration device has an access to the closed volume beneath the sealing edge in order to allow the connection to be released.

An evacuation pump can be fluidically connected to the closed volume in order to ensure initial evacuation or maintenance of the negative pressure even in a static state. The evacuation pump can be operable in pressure operation in order to fill the closed volume, and in pressure operation, the pump then serves as an aeration device for introducing air.

A receiving bowl having a concave curvature can be arranged at the distal end of the prosthesis socket. On account of the convex curvature of the suction cup, that is to say a curvature which is directed away from the liner, and a receiving bowl that has an opposite curvature and may be manufactured as a separate component or be an integral constituent of the prosthesis socket, a covering function of the suction cup arises prior to the introduction or prior to the deformation of the suction cup at the contact region or on the receiving bowl. In the case of a concave curvature of the receiving bowl or of the contact region, it is possible for a very large suction cup diameter to be used since the elastic suction cup then deforms and assumes an opposite curvature, specifically a concave curvature. On account of the large suction cup area that is possible as a result, a correspondingly large holding force arises with respect to a relatively small suction cup surface at a constant negative pressure. The receiving bowl can have an inwardly projecting ring or protrusion in order to effect additional mechanical locking of the turned over suction cup counter to being pulled out of the contact region, the receiving bowl or the prosthesis socket.

A fluidic connection can exist between the receiving space within the prosthesis liner and the closed volume between the suction cup and the prosthesis socket in the contact region, it being possible for said fluidic connection to have a blocking device which prevents a return flow into the receiving space. As a result, it is possible and provision is made for an evacuation pump to be assigned to the prosthesis socket and in particular to be arranged thereon in order to evacuate the volume between the prosthesis socket and the suction cup.

A surface with a roughened structure, a textile and/or a non-adhesive or air-permeable coating, which is formed in a manner corresponding to the surface property within the sealing lip, may be provided in the contact region of the prosthesis socket. This structure or coating in the contact region is surrounded by a region in which the sealing lip can bear in a sealing manner; optionally, the air-permeability and thus the targeted non-adhesion is formed by the coatings or structures on the suction cup and the contact region interacting.

BRIEF DESCRIPTION OF THE DRAWINGS

Exemplary embodiments of the invention are explained in more detail in the following text with reference to the appended figures. Identical reference signs denote identical components. In the figures:

FIG. 1 shows a schematic illustration of a side view of a prosthesis liner and of a suction cup;

FIG. 2 shows a perspective illustration according to FIG. 1;

FIG. 4 shows a sectional view through a prosthesis liner during joining;

FIG. 5 shows a sectional view in the joined state;

FIG. 6 shows a sectional illustration of a suction cup;

FIG. 7 shows a perspective illustration of a prosthesis liner with a suction cup prior to joining to a receiving bowl;

FIG. 8 shows a sectional view of FIG. 7;

DETAILED DESCRIPTION

Figure 3:
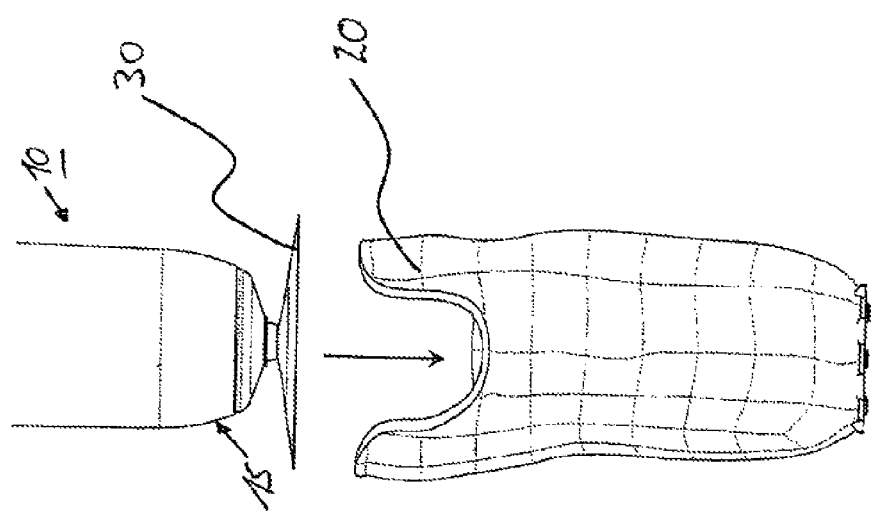
FIG. 3 shows a side view of a prosthesis socket and of a prosthesis liner prior to joining.

FIG. 1 shows a prosthesis liner 10 having an elastic main body 11 which can be produced for example from silicone or some other elastomer. Provided at the proximal end 12 of the prosthesis liner is an opening through which a prosthesis user can fit his stump into a receiving space within the prosthesis liner 10. The receiving space is not shown in this figure. Placing the prosthesis liner usually takes place by rolling the proximal end 12 down or turning the proximal end 12 inside out, placing a distal end 14 of the prosthesis liner against the distal end of the stump and subsequently rolling it onto the stump. In the illustrated example, a dimensionally stable end cap 16 is arranged at the distal end 14 of the prosthesis liner 10, said end cap 16 serving to stably and gently bed the stump with respect to the connection of a suction cup 30 to the outer side 15, that is to say that side of the prosthesis liner 10 that is located away from the receiving space. Fastening devices 160, via which it is possible to arrange the suction cup 30, which is provided with a curvature formed in the distal direction away from the liner 10, on the end cap 16, are arranged on the end cap 16. The suction cup 30 likewise has a fastening device 316 via which the suction cup 30 is securable to the prosthesis liner 10, in particular to the distal end cap 16.

The underside of the suction cup 30 can be seen in FIG. 2, and the sealing lip 31 on the outer circumference of the suction cup 30 can likewise be seen. As a result of the sealing lip 31 being arranged on the outer circumference of the suction cup 30, a maximum area is provided, such that, even in the event of a relatively low negative pressure, a high holding force can be realized. The suction cup 30 is fastenable reversibly to the prosthesis liner 10 via the fastening elements 160, 316. As a result, it is possible to secure different types of suction cup to the liner. The suction cups 30 can differ in terms of their diameter, shape or selection of material.

The coupling of the suction cup 30 to the prosthesis liner 10 is preferably embodied as a mechanical coupling, for example as a screw coupling, and it is likewise possible for an adhesive connection to be formed between the components. As an alternative to a separate configuration of the suction cup 30, it is possible to integrate the latter directly into the distal end cap 16, for example to integrally mold it or to injection-mold it as part of a two-component injection molding process. The end cap 16, which is also deformable to a certain degree, can be manufactured from the material of the prosthesis liner 10 and, in the event of a cohesive connection to the suction cup 30, form a coherent system between the prosthesis liner 10 and the suction cup 30.

FIG. 3 illustrates the application of the prosthesis liner 10 with the suction cup 30 arranged on the outer side 15 thereof and fastened thereto, in conjunction with a prosthesis socket 20. The prosthesis socket 20 substantially follows the outer contour of the stump (not illustrated) and, in the exemplary embodiment illustrated, is formed from a dimensionally stable airtight material, for example a fiber-reinforced plastics material. The user fits his stump, with the prosthesis liner 10 and the suction cup 30 reversibly fastened to the distal end 14, through the proximal opening of the prosthesis socket 20 and into the latter, with the result that, as a result of the application of bodyweight in the distal direction, a force is applied to the suction cup 30. Even if the suction cup 30, as embodied in the illustrated example, has a larger outside diameter than the inside diameter of the prosthesis socket 20, the suction cup 30 can be introduced into the prosthesis socket 20 since the suction cup 30 is made of an elastic material, for example from a TPE, and so in this case a deformation of the suction cup 30 occurs. As a result of the bodyweight, the suction cup 30 that is provided in the initial state with a convex contour directed away from the prosthesis liner 10 (i.e., the surface facing toward the liner 10 is convex shaped) is turned over and so the sealing lip 31 bears against the inner side of the prosthesis socket 20, forming a sealing edge. A comparison between FIG. 3 and FIG. 5 (described below) illustrates the surface of the suction cup 30 facing toward the prosthetic liner 10 being completely inverted from a convex shape to a concave shape when inserted into prosthetic socket 20. Bearing takes place against the entire inner contour of the prosthesis socket 20, such that a volume is enclosed between the suction cup 30 and the prosthesis socket. The air enclosed within the prosthesis socket 20 is pushed out in the direction of the arrow past the sealing lip 31 during the introduction of the prosthesis liner 10, since the prosthesis socket 20 is formed in an airtight manner and has a closed distal end.

Therefore, a volume is defined between the suction cup and the prosthesis socket inner side, it being possible for said volume to be evacuated by application of force in the distal direction. As a result of the negative pressure that is produced, for example in a swing phase, a holding force is produced between the suction cup 30 and the prosthesis socket 20 such that the prosthesis liner 10, which bears in an adhering manner against the skin of the stump, is held against the prosthesis socket 20 via the suction cup 30, to which the prosthesis liner 10 is mechanically coupled.

The sectional illustration in FIG. 4 shows a partially introduced prosthesis liner 10 with the distal end cap 16 and the suction cup 30 introduced into the prosthesis socket 20. The receiving space 13 for the stump of the prosthesis user is also shown in the sectional illustration. As a result of the pressure movement in the distal direction, the suction cup 30 is moved, together with the prosthesis liner 10, in the direction of the distal end 22 of the prosthesis socket 20. The closed volume 50 provided between the suction cup 30 and the distal end 22 is compressed, the gas, generally air, contained within the volume 50 is pushed out and the prosthesis liner 10 can be pushed further in the direction of the distal end 22 of the prosthesis socket 20 until the suction cup 30 reaches the contact region 21 located at the distal end 22.

FIG. 5 illustrates the end position of the prosthesis liner 10 and thus also of the suction cup 30 within the prosthesis socket 20. The volume 50 is minimized, and the sealing lip of the suction cup 30 bears against the contact region 21 such that in the event of loading in the proximal direction an increase in volume is brought about, this resulting in the negative pressure produced exerting a holding force over the area of the suction cup 30, such that the prosthesis liner 10 is held reliably in the prosthesis socket 20.

FIG. 6 shows a sectional illustration of the suction cup 30 in a detail illustration. In addition to the fastening means 316 in the form of an incorporated thread, the convex curvature of the unloaded, non-introduced suction cup 30 can be readily seen. Formed on the underside of the suction cup 30 are a number of circumferential sealing lips 31 which are arranged in the form of a lamellar structure. The sealing lips 31 are arranged concentrically with one another and increase the security in that at least one sealing lip 31 always bears as a sealing edge in radially sealing contact with the inner side of the prosthesis socket 20 or against the contact region 21. A rough structure or a fabric on the suction cup surface 32 can be arranged or formed on the surface of the underside of the suction cup 30, thereby ensuring that only the sealing lip 31 that is desired in each case comes into sealing contact with the prosthesis socket 20 and the effective area of the vacuum is distributed over the entire area of the underside. The underside of the suction cup 30 can thus not pass unintentionally into sealing contact with the prosthesis socket 20 at some other location, and so uniform distribution of the sealing force and a minimum level of the holding force are always achieved.

The prosthesis liner 10 having the end cap 16 and suction cup 30 mounted thereon in a not-yet-joined position relative to the receiving bowl 23 is illustrated in a perspective illustration in FIG. 7. The receiving bowl 23 can be produced for example of a light metal or a plastics material and forms the distal termination of the prosthesis socket 20 (not illustrated further). At its lower, distal end, the receiving bowl 23 can have connection devices for additional components, for example threads or the like, in order to fasten upper parts of a prosthetic joint thereto. The receiving bowl 23 is equipped with an aeration device 52 in the form of a nonreturn valve in order to push enclosed air out of the volume between the suction cup 30 and the receiving bowl 23 and, in the event of a desired detachment of the prosthesis socket 20, to be able to fill the closed volume with air again. The inside diameter of the receiving bowl 23 corresponds substantially to the outside diameter of the suction cup 30. The suction cup 30 can also be configured with a slightly larger or smaller outside diameter. If the outside diameter is larger, the volume is already closed on coming into contact with the upper periphery of the receiving bowl 23; if the outside diameter corresponds to the inside diameter of the receiving bowl 23, the volume is closed off only during the further progress of the introduction movement, when the suction cup 30 has arrived in a region of the receiving bowl 23 in which the receiving bowl 23 narrows toward the distal end. The inner contour of the receiving bowl 23 is formed in a cup- or tub-like manner, wherein the side walls of the receiving bowl 23 extend substantially perpendicularly downward at the proximal periphery but then narrow further in the distal direction.

The position of the suction cup 30 above the receiving bowl 23 can be seen in a sectional illustration in FIG. 8. Likewise, the inclined wall of the receiving bowl 23, which extends conically from the upper, proximal periphery in a manner tapering toward the distal bottom, can be seen in the embodiment illustrated in FIG. 8. The aeration device 52 represents a closeable connection to the surrounding atmosphere. At its distal end 12, the prosthesis liner 10 having the elastic main body 11, which can be formed for example from silicone or a polymer, has the end cap 16, which can be integrally formed on the elastic main body 11 or be fastened thereto in some other way. The suction cup 30 having the sealing lip 31 extending around the outer circumference has a convex contour that is curved away from the main body 11 in the illustrated initial state, said contour being able to close off an air volume together with the receiving bowl 23.

Figure 9:
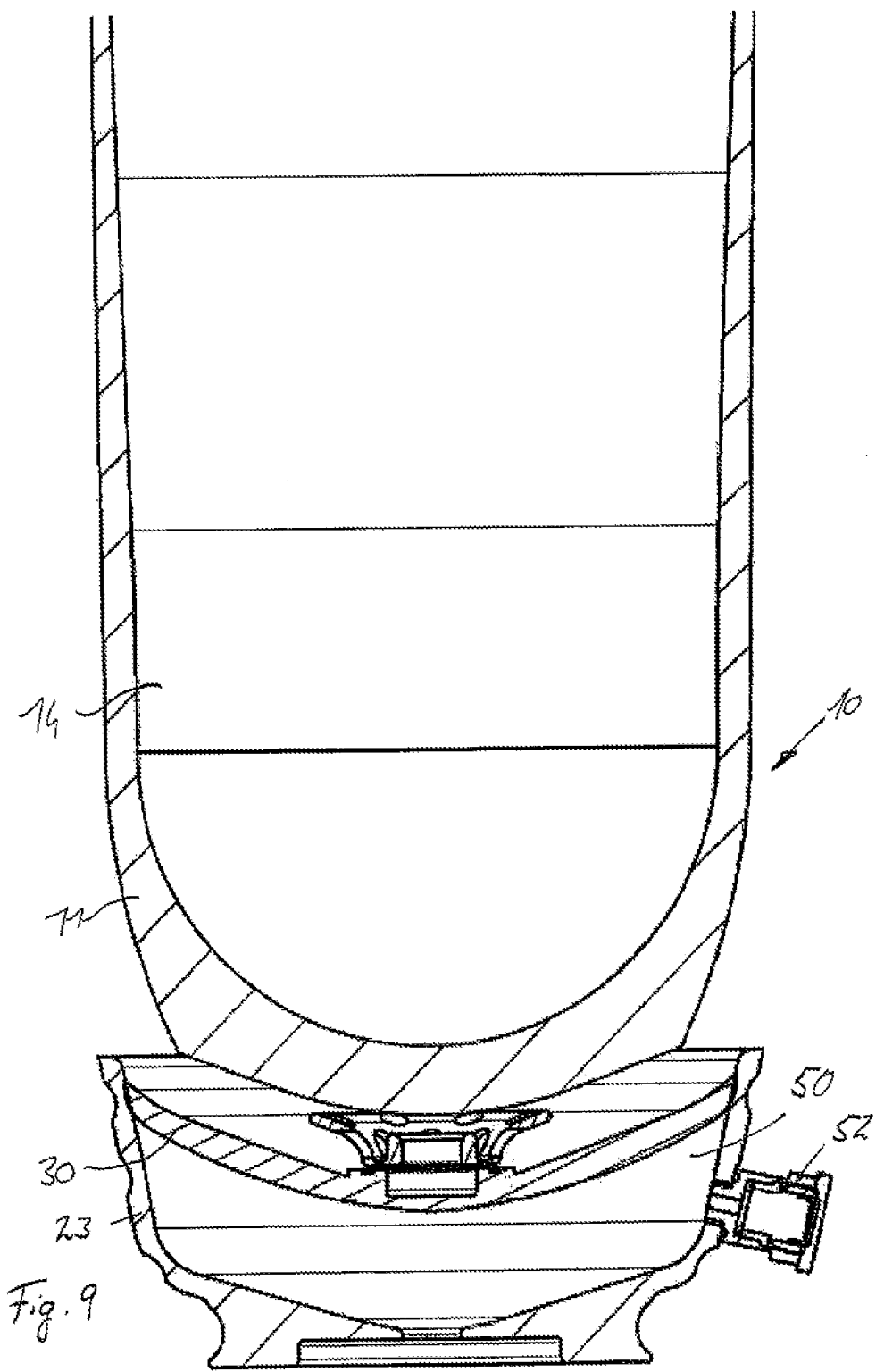
FIG. 9 shows an illustration according to FIG. 8 during joining.

The partially introduced state of the suction cup 30 into the receiving bowl 23 is shown in FIG. 9. The outer circumference having the sealing lip 31 of the suction cup 30 is already bearing in a sealing manner against the inner surface of the receiving bowl 23 and closes the volume 50 off toward the outside. Since the outer sealing lip 31 was already bearing against the upper periphery of the receiving bowl 23, as a result of the further introduction of the prosthesis liner 10, a central force in the introduction direction is exerted on the elastic suction cup 30 via the central fastening device, this resulting in the suction cup 30 turning or bending over. In the position according to FIG. 9, the surface of the suction cup 30 facing toward the prosthesis liner 10 is shown completely inverted from the convex shape shown in FIG. 8 to a concave shape after being inserted into the receiving bowl 23, and the volume 50 enclosed between the suction cup 30 and the receiving bowl 23 is fluidically connected to the aeration device 52, which can at the same time be configured as a venting device.

Figure 10:
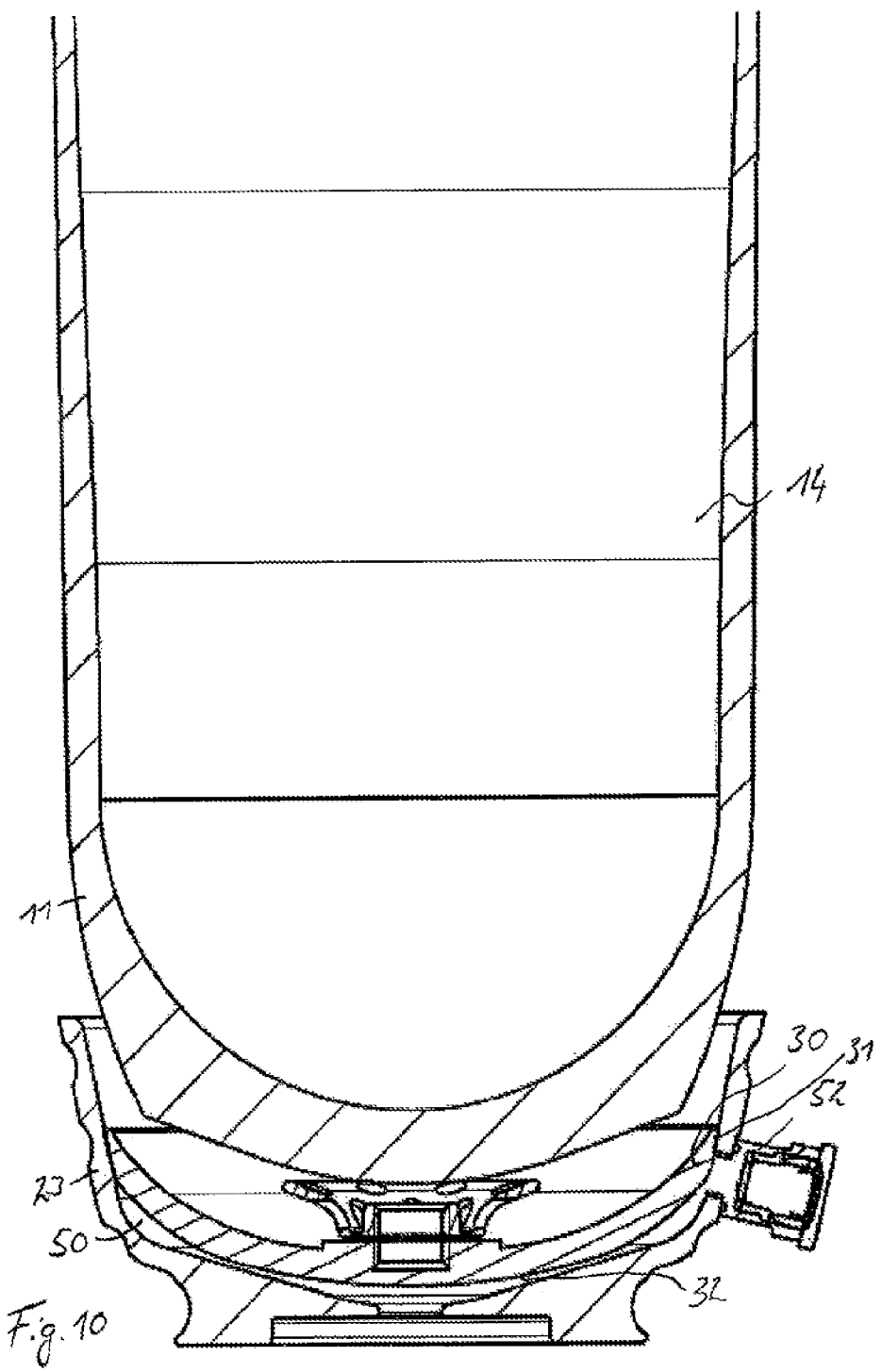
FIG. 10 shows an illustration according to FIG. 8 in the joined state.

FIG. 10 illustrates the completely introduced state of the prosthesis liner 10 and of the suction cup 30 into the receiving bowl 23. The enclosed volume 50 is minimal, and the outer circumference and the sealing lip 31 bear around the entire circumference and in a sealing manner against the inner side of the receiving bowl 23, but the volume 50 is still fluidically connected to the aeration device 52. If the aeration device 52 is closed, on account of the airtight termination at the circumference of the suction cup 30, the prosthesis liner 10 can be separated from the receiving bowl 23 only under very high forces counter to the holding force by the positive pressure on the outer side of the suction cup. The surface 32 of the suction cup 30 and/or of the receiving bowl 23 can be provided regionally with a non-adhesive or air-conducting or roughened structure, in order to prevent the suction cup 30 also enclosing a volume at other locations apart from at the desired outer circumference. Instead of the separate receiving bowl 23, the suction cup 30 and the prosthesis liner 10 can also be introduced directly into a correspondingly formed prosthesis socket 20 which can be produced from a fiber-reinforced plastics material or a similar material. As a result of the suction cup 30 turning over from the original convex shape into a concave shape, enhanced contact pressure of the sealing lip 31 against the inner wall or against the contact region 21 is also brought about on account of the restoring forces in addition to the holding force by the positive pressure.

Figure 11:
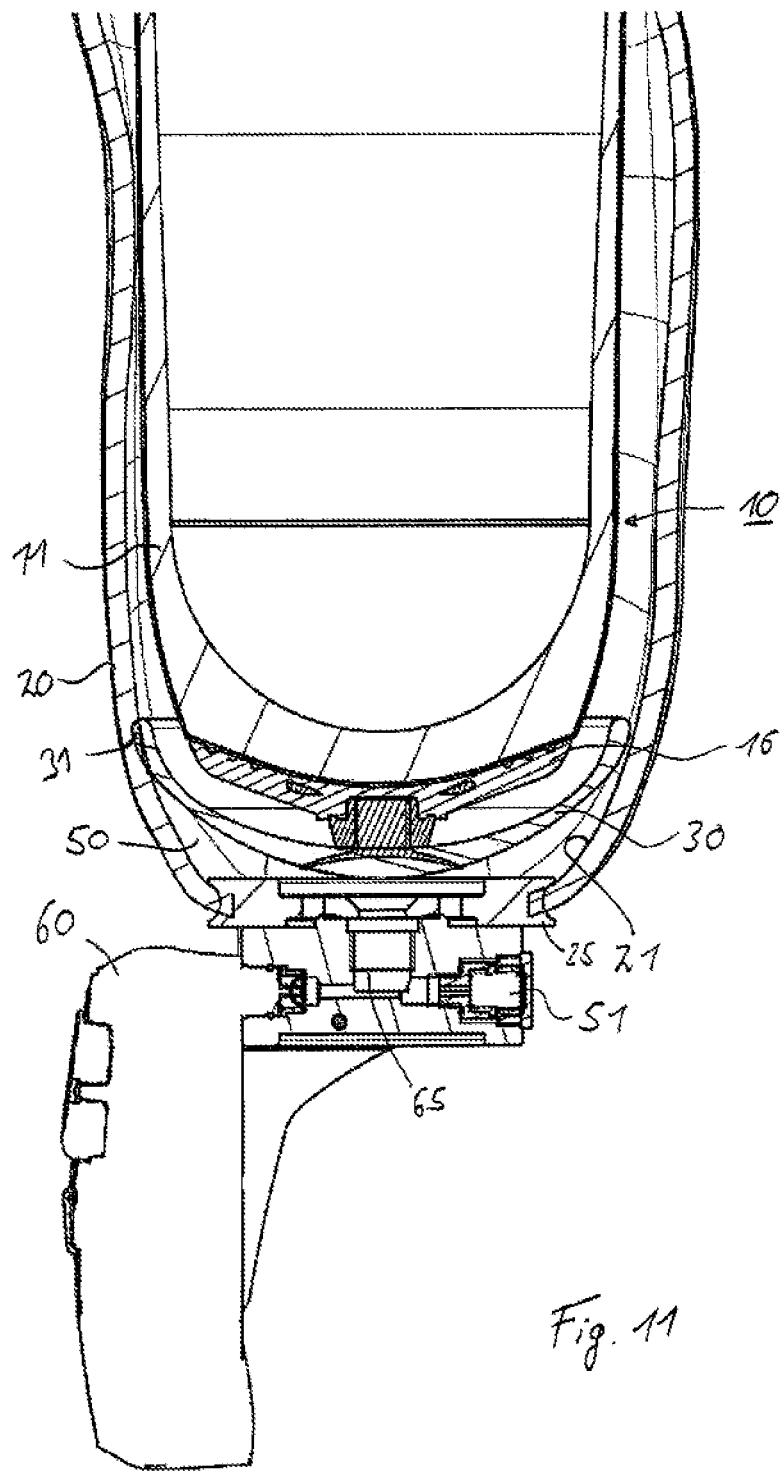
FIG. 11 shows a sectional illustration of a prosthesis socket system having a pump.

A variant of the invention is illustrated in FIG. 11 in which the prosthesis liner 10 is illustrated in a manner introduced into the prosthesis socket 20. It can be seen in the sectional illustration that the suction cup 30 has been turned over from the convex shape into the concave shape. The sealing lip 31 bears in a sealing manner against the contact region 21 on the inner side of the prosthesis socket 20. Attached to the distal end is a connection disk 25 to which a vacuum pump 60 is fastened. The vacuum pump 60 is fluidically connected to the volume 50 via a duct 65. A nonreturn valve can be arranged between the connection disk 25 and the duct 65 in order to avoid a return flow of pushed-out air. In order to release the connection between the prosthesis socket 20 and the suction cup 30 it is then necessary to activate an aeration device. If a nonreturn valve is not arranged in the connection disk 25, the enclosed volume 50 is extended by the duct 65. The air can then be drawn off out of the volume 50 via the evacuation pump 60. In order to insert the suction cup 30 more easily, provision is made of a blocking device 51 in the form of a nonreturn valve, through which air can be ejected so that it is not necessary for all of the air to be transported out of the prosthesis socket 20 via the vacuum pump 60. In order to aerate the volume 50, the vacuum pump 60 can also be operable in pressure operation so that air can be introduced into the volume 50. To this end, it is then necessary to block the venting valve 51 so that air can be pushed into the enclosed volume 50. In principle, it is necessary for provision to be made of an aeration device which is located beneath the sealing edge between the suction cup 30 and the prosthesis socket 20 in order to be able to allow aeration of the evacuated volume 50 and thus to remove the stump from the prosthesis. In the illustrated exemplary embodiment, the negative pressure is broken down and the enclosed volume 50 is flooded by way of the distal access via the valve 51 and the duct 65.

Figure 12:
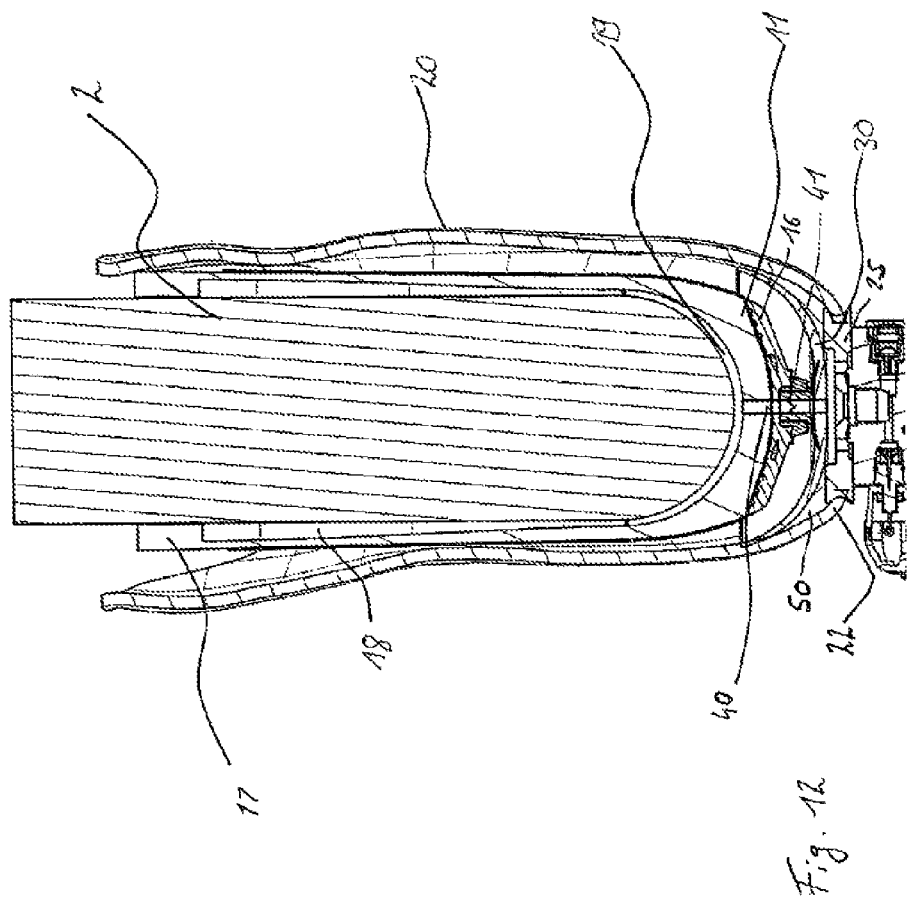
FIG. 12 shows a sectional view of a variant of the invention.

FIG. 12 is a variant of FIG. 11, in which the arrangement beneath the connection disk 25 is configured in an identical manner and is not illustrated further. The prosthesis liner 10 has, at its proximal end, a section 17 that provides sealing with respect to the stump 2 and functions as a sealing lip. In the distal direction, the sealing lip, which is configured in a circumferential manner, is adjoined by a set-back region 18 which can be provided with a material or a fabric coating or else only forms a clearance in order to allow the buildup of a negative pressure in this intermediate region. Such an intermediate region can also be provided by the placement of a textile over the stump 2 in this region. In this case, it is necessary to ensure that the sealing section 17 bears against the stump 2 in a sealing manner. The clearance 19 between the stump 2 and the inner side of the prosthesis liner 10 is fluidically connected via a duct 40 to the evacuated volume 50 and via the duct 65 to the vacuum pump 60. As a result, it is possible to produce a negative pressure between the stump 2 and the prosthesis liner 10 via the vacuum pump 60. The volume 50 can be separated from the volume 19 between the stump 2 and the liner 10 via a nonreturn valve 41, so that a return flow into the volume 19 between the stump 2 and the liner 10 is prevented.

A configuration according to FIG. 12 has the advantage that what is referred to as the milking effect is reduced, said effect occurring when a tensile force is applied to the distal end 22 of the prosthesis socket 20. As a result of the negative pressure being present extensively in the entire stump region, the introduction of forces at the stump is improved and fluctuations in volume are reduced. Since the negative pressure is not present between the prosthesis socket 20 and the prosthesis liner 10 but between the suction cup 30 and the prosthesis socket 20, the prosthesis socket 20 does not have to have the high requirements with regard to fitting precision and impermeability that are placed on the conventional negative-pressure sockets.

As a result of the elasticity of the prosthesis liner, the latter molds itself optimally to the stump contour on account of the effective negative pressure, without in the process causing pressure sores or hematomas.

Figure 13:
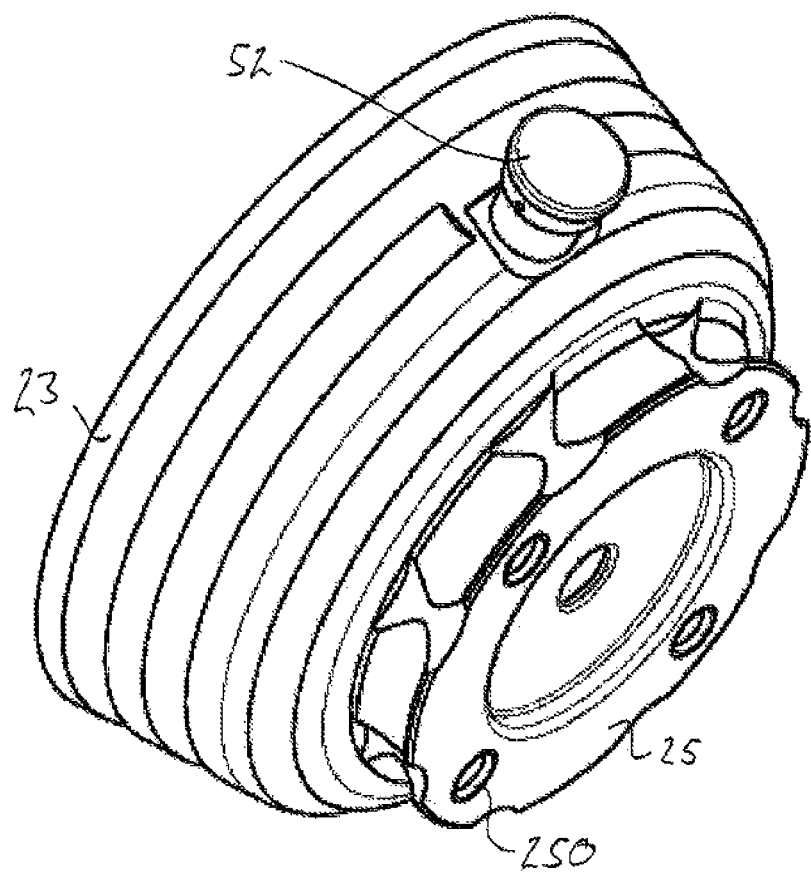
FIG. 13 shows a perspective view of a receiving bowl obliquely from below.

FIG. 13 illustrates a perspective bottom view of the receiving bowl 23 with the aeration device 52 and the connection disk 25. Threads 250 can be arranged in the connection disk 25 for example in order to be able to fasten a vacuum pump 60 or other components of a prosthetic fitting.

Figure 14:
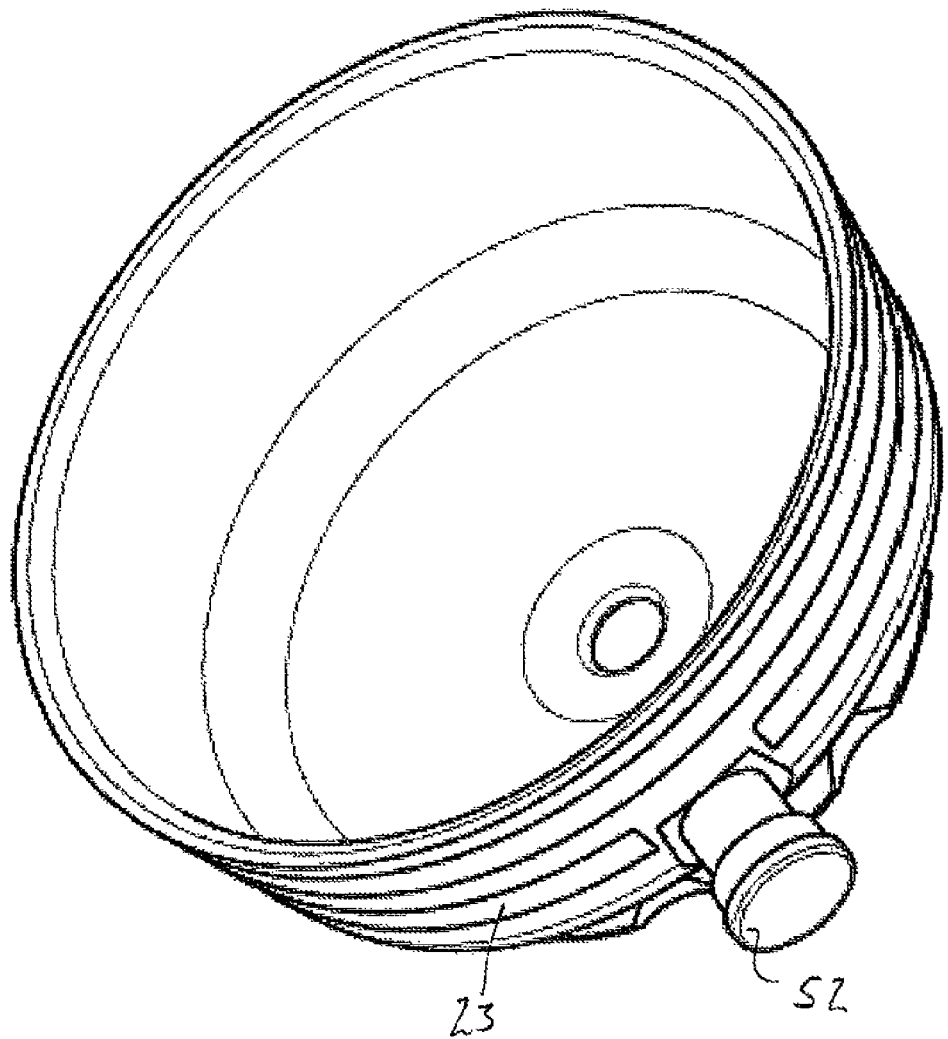
FIG. 14 shows a perspective illustration of a receiving bowl obliquely from above.

FIG. 14 shows an oblique plan view of the receiving bowl 23, wherein the conically extending side walls and the cup-shaped design and the distal closed configuration with the option of introducing a through-bore for a connection to a vacuum pump 60 can be seen.

Figure 15:
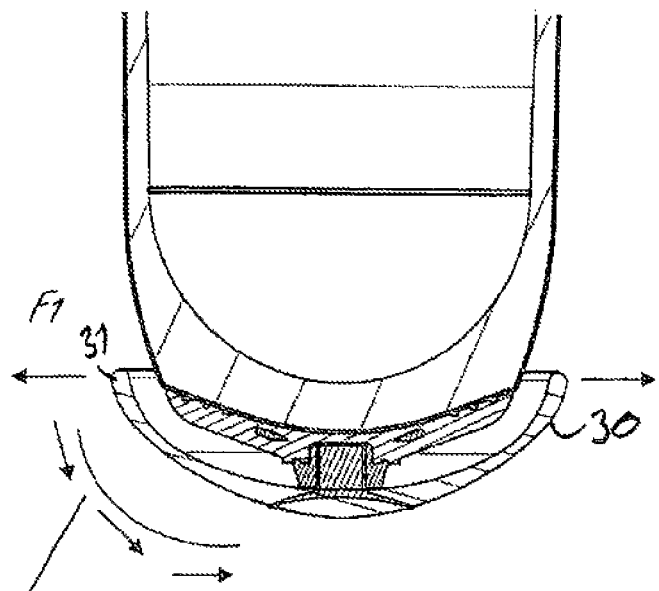
FIG. 15 shows a detail illustration of a prosthesis liner having a suction cup in the joined state.
Figure 16:
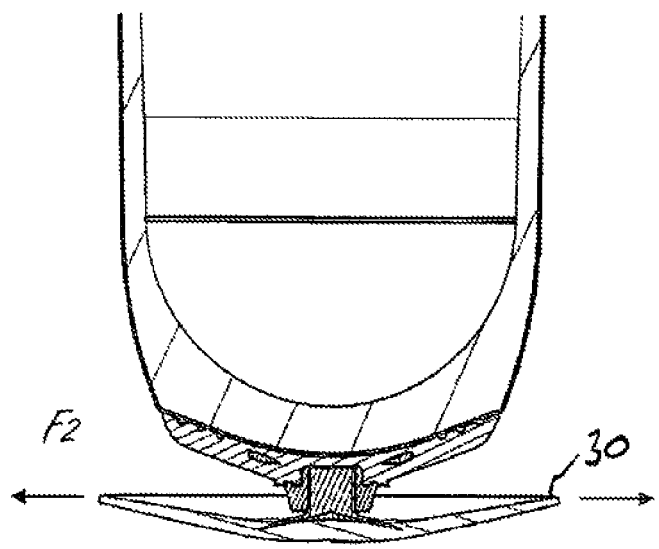
FIG. 16 shows an illustration according to FIG. 15 during the removal of the suction cup.

FIG. 15 schematically illustrates the mechanisms of the placement of the suction cup 30 on the receiving bowl 23 or contact region 21 of the prosthesis socket 20. If the pressure in the evacuated volume 50 between the suction cup 30 and the prosthesis socket 20 drops for any reason, this results in an increased clearance between the suction cup 30 and the prosthesis socket 20. In the event of loading of the prosthesis in the distal direction, for example in a swing phase, this results in the prosthesis liner 10 being easily moved out of the prosthesis socket 20, this resulting in a rolling movement of the turned-over sealing lip 31, with the result that the latter is pressed more firmly against the socket wall (not illustrated) or wall of the receiving bowl 23, with the result that the sealing action is further increased. This function results in increased loss prevention, which originates from the turned-over contour from originally convex to concave in the mounted state. In FIG. 15, the suction cup 30 is still located in the completely introduced position, the sealing force F1 on the inner side of the prosthesis socket 20 is relatively low and results from the restoring forces on account of the elastic deformation on turning over the suction cup 30. If the prosthesis socket 20 is moved in the distal direction relative to the suction cup 30, the central region of the suction cup 30 is lifted and is located level with the sealing lip 31, with the result that the sealing force F2 increases substantially. FIG. 15 shows the state when the prosthesis liner 10 sits in the prosthesis socket 20 without a clearance, and FIG. 16 shows the state when a clearance is present between the prosthesis socket 20 and the liner 10. In the event of reoccurrence and distal movement of the prosthesis liner 10 into the prosthesis socket 20, the air enclosed in the volume 50 is pushed out and the holding force increased again.

Compared with mechanical peg locking mechanisms, the illustrated invention has the advantage of a smaller structural height. The prosthesis socket system can thus also be used where the use of what are referred to as shuttle-lock systems is not possible. The holding force with respect to the distal prosthetic devices is produced via the prosthesis socket 20 between the inside thereof and the fastening system composed of the suction cup 30 and the prosthesis liner 10. The suction cup 30 is held on the prosthesis liner 10 via a mechanical coupling element, adhesive bonding or a one-piece configuration. The region, proximally adjoining the suction cup 30, of the prosthesis liner 10 no longer has to rest against the prosthesis socket 20 in an airtight manner. Since the negative pressure is no longer present directly between the prosthesis liner 10 and the prosthesis socket 20, but rather the additional device in the form of the suction cup 30 in conjunction with the prosthesis socket 20 applies the holding force, the fitting precision of the prosthesis socket 20 and the fastening to the prosthesis socket 20 are always ensured, regardless of fluctuations in volume of the stump 2. If the negative pressure between the prosthesis liner 10 and the socket inner wall builds up, this can result in the sealing contact being able to be interrupted in the event of fluctuations in the volume of the stump 2, and this would result in turn in the detachment of the prosthesis socket 20 from the prosthesis liner 10.

On account of the fact that the suction cup 30 is arranged only at the distal end of the prosthesis liner 10, the prosthesis liner 10 is not necessarily brought into direct contact with the inner side of the prosthesis socket 20, with the result that the prosthesis liner 10 is mechanically loaded less. The same goes for the soft tissue on the stump 2 of the prosthesis user, such that the formation of hematomas is avoided.

The invention claimed is:

1. A prosthesis liner for placing on a stump, comprising:
   an elastic main body which has a proximal opening and a distal end, the proximal opening configured to introduce the stump into a receiving space;
   a first fastening device on an outside of the distal end of the main body;
   at least one suction cup, the at least one suction cup having a concave shape on a side facing away from the main body prior to use, the at least one suction cup completely inverting from the concave shape prior to use to a convex shape when inserted into a receiving bowl of a prosthetic socket, a closed volume being formed between the at least one suction cup and the receiving bowl;
   a second fastening device provided on a top side of the suction cup, wherein the first and second fastening devices couple the top side of the at least one suction cup to the distal end of the main body on an outside of the prosthesis liner.

2. The prosthesis liner as claimed in claim 1, wherein the suction cup is configured as a separate component and fastened to the prosthesis liner.

3. The prosthesis liner as claimed in claim 1, wherein the suction cup is fastened reversibly to the distal end.

4. The prosthesis liner as claimed in claim 1, further comprising a semi-deformable, stable end cap arranged at the distal end.

5. The prosthesis liner as claimed in claim 1, wherein the suction cup includes a plurality of circumferential sealing lips positioned on the side facing away from the main body.

6. The prosthesis liner as claimed in claim 1, further comprising a fluidic connection between the receiving space and the suction cup.

7. The prosthesis liner as claimed in claim 6, further comprising a blocking device, which prevents a return flow into the receiving space, is arranged in the fluidic connection.

8. The prosthesis liner as claimed in claim 1, further comprising a section that provides sealing with respect to the stump is formed at a proximal end of the prosthesis liner, and a recessed region, the recessed region provided with at least one of a rough structure, channels, a textile, a foam, or air-permeable coating arranged distally to said section.

9. The prosthesis liner as claimed in claim 1, wherein the at least one suction cup completely inverts from the concave shape to the convex shape when inserted into the receiving bowl.

10. A prosthesis socket system, comprising:
    a prosthesis liner, the liner comprising:
      an elastic main body having a proximal opening and a distal end, the proximal opening configured to receive a residual limb into a receiving space;
      a first fastening device on an outside of the distal end of the main body;
      at least one suction cup;
      a second fastening device positioned on a top side of the at least one suction cup, wherein the first and second fastening devices couple the top side of the at least one suction cup to the distal end of the main body on an outside of the prosthesis liner;
    a prosthesis socket, the socket comprising:
      a proximal opening to receive the liner;
      a receiving bowl positioned at an interior distal end of the socket;
      a closed volume formed between the at least one suction cup and the receiving bowl;
      wherein the at least one suction cup completely inverts from a concave shape before insertion of the liner into the socket to a convex shape when the liner is positioned in the socket.

11. The prosthesis socket system of claim 10, wherein the closed volume is fluidically connected to at least one blocking device, said fluidic connection allowing air to flow out and preventing a return flow.

12. The prosthesis socket system of claim 10, wherein the closed volume is fluidically connected to an aeration device for introducing air.

13. The prosthesis socket system as claimed in claim 10, further comprising an evacuation pump fluidically connected to the closed volume.

14. The prosthesis socket system as claimed in claim 13, wherein the evacuation pump is reversibly operable to fill the closed volume.

15. The prosthesis socket system of claim 10, wherein a fluidic connection exists between the receiving space and the closed volume.

16. The prosthesis socket system of claim 15, further comprising a blocking device, which prevents a return flow into the receiving space, arranged in the fluidic connection.

17. The prosthesis socket system of claim 10, wherein at least one of a surface with a roughened structure, a textile or a non-adhesive coating is provided in the receiving bowl.

18. The prosthesis socket system of claim 10, wherein the suction cup includes a plurality of circumferential sealing lips positioned on the bottom side of the at least one suction cup.

19. A prosthesis liner for placing on a stump, comprising:
    an elastic main body having a proximal opening and a distal end, the proximal opening configured to receive the stump into a receiving space;
    at least one suction cup, the at least one suction cup being arranged on an outer side of the prosthesis liner, the at least one suction cup completely inverting from a concave shape prior to use to a convex shape during use, at least one closed volume being established between the at least one suction cup and a contact region of a receiving bowl of a prosthetic socket during use, the at least one closed volume comprising a negative pressure;
    a blocking device arranged in flow communication with the at least one closed volume to maintain the negative pressure;
    at least one fastening device connecting the at least one suction cup to an outside of the distal end of the main body.

20. The prosthesis liner as claimed in claim 19, wherein the at least one suction cup has a concave shape on the side facing away from the prosthesis liner prior to use.

21. A prosthesis socket system, comprising:
    a prosthesis liner, the liner comprising:

an elastic main body having a proximal opening and a distal end, the proximal opening configured to receive the stump into a receiving space;

at least one suction cup, wherein the at least one suction cup is arranged on an outer side of the prosthesis liner, the at least one suction cup having a concave shape on a side of the at least one suction cup facing away from the main body prior to use and being configured to completely invert to a convex shape during use;

at least one fastening device connecting the at least one suction cup to an outside of the distal end of the main body;

a prosthesis socket, the prosthesis socket comprising:

a proximal opening to receive the liner;

a receiving bowl positioned at an interior distal end of the socket, the receiving bowl having an inner sidewall surface, the at least one suction cup forming a seal with the inner sidewall surface when the liner is inserted into the socket;

a closed volume formed between the at least one suction cup and the receiving bowl, wherein the closed volume comprises a negative pressure;

a first blocking device arranged in flow communication with the at least one closed volume to maintain the negative pressure.

22. The prosthesis socket system of claim 21, wherein a fluidic connection exists between the receiving space and the closed volume.

23. The prosthesis socket system of claim 22, further comprising a second blocking device arranged in the fluidic connection, which prevents a return flow into the receiving space.

24. The prosthesis liner as claimed in claim 21, wherein the at least one suction cup completely inverts from the concave shape to the convex shape when inserted into the receiving bowl.

* * * * *